United States Patent
Seifert et al.

(10) Patent No.: US 6,211,379 B1
(45) Date of Patent: Apr. 3, 2001

(54) PROCESS FOR PREPARING HETEROCYCLIC COMPOUNDS

(75) Inventors: Hermann Seifert, Bergisch Gladbach; Reinhard Lantzsch, Wuppertal; Werner Lindner, Köln; Klaus Jelich, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/488,436

(22) Filed: Jan. 20, 2000

(30) Foreign Application Priority Data

Jan. 28, 1999 (DE) .............................. 199 04 310

(51) Int. Cl.$^7$ ................................. C07D 417/06
(52) U.S. Cl. ....................................... 546/280.1
(58) Field of Search ............................... 546/280

(56) References Cited

U.S. PATENT DOCUMENTS

| | | | |
|---|---|---|---|
| 4,616,025 | 10/1986 | Ezer et al. ........................... | 514/342 |
| 4,849,432 | * 7/1989 | Shiokawa ............................ | 514/341 |
| 4,988,712 | * 1/1991 | Shiokawa ............................ | 514/340 |

FOREIGN PATENT DOCUMENTS 2126222 3/1984 (GB) .

* cited by examiner

*Primary Examiner*—Robert Gerstl

(74) *Attorney, Agent, or Firm*—Joseph C. Gil

(57) ABSTRACT

The present application relates to a process for preparing compounds of the formula (I)

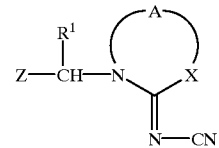

(I)

in which $R^1$, A, X and Z are each as defined in the description by reacting compounds of the formula (II)

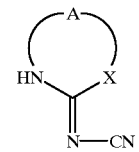

(II)

in which A and X are each as defined in the description with compounds of the formula (III)

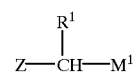

(III)

in which Z, $R^1$ and $M^1$ are each as defined in the description.

2 Claims, No Drawings

PROCESS FOR PREPARING HETEROCYCLIC COMPOUNDS

The present invention relates to a novel process for preparing known heterocyclic compounds by alkylation of suitable precursors.

Such alkylation reactions in aprotic solvents are known (EP A2 0235 725).

Also known is the preparation of unsaturated heterocyclic compounds by alkylating unsubstituted ring nitrogen atoms which can be carried out, inter alia, in alcohols (EP A2 0 259 738).

In these instances, a subsequent purification of the product is required to achieve a sufficient purity; moreover, the yields that can be obtained with the known processes are unsatisfactory.

It has now been found that compounds of the formula (I)

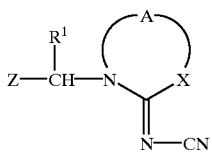

(I)

in which

R¹ represents a hydrogen atom or an alkyl group,

A represents an ethylene group, which may be substituted by alkyl, or a tri-methylene group, which may be substituted by alkyl, X represents an oxygen or sulphur atom or the group

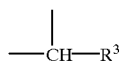

in which

R³ represents a hydrogen atom or an alkyl group, and

Z represents an optionally substituted 5- or 6-membered heterocyclic group which contains at least two heteroatoms selected from the group consisting of oxygen, sulphur and nitrogen atoms, or denotes an optionally substituted 3- or 4-pyridyl group, are obtained when compounds of the formula (II)

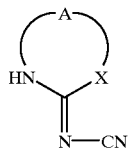

(II)

in which

A and X are each as defined above are reacted with compounds of the formula (III)

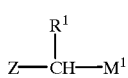

(III)

in which

R¹ and Z are each as defined above and

M¹ represents a halogen atom or the group —OSO₂—M², in which

M² denotes a lower alkyl group, an aryl group or OM³, where

M³ denotes a lower alkyl group or an alkali metal, in the presence of a protic solvent and, if appropriate, in the presence of a base, followed by crystallization from an alcohol.

The process according to the invention avoids the purification step of recrystallization which has hitherto been necessary and requires one operation less than the processes of the prior art.

Surprisingly, the yields obtained in the process according to the invention are considerably higher than the yields that can be obtained in the processes of the prior art.

Although in the process according to the invention the reaction of the compounds (III) and (II) is carried out in protic solvents, contrary to expectations an ether formation according to Williamson (see textbooks of organic chemistry) is not observed.

In the general formulae I, II and III,

R¹ preferably represents hydrogen or a C₁–C₃-alkyl group, particularly preferably hydrogen;

A preferably represents an ethylene or trimethylene group, which may in each case be substituted by a C₁–C₃-alkyl group, particularly preferably an ethylene group;

X preferably represents an oxygen or sulphur atom, particularly preferably a sulphur atom;

Z preferably represents a halogenated 5- or 6-membered heterocyclic group which contains 2 heteroatoms selected from the group consisting of oxygen, sulphur and nitrogen or represents a halogenated 3- or 4-pyridyl group, particularly preferably a halogenated thiazolyl or 3-pyridyl group, very particularly preferably 2-chloro-pyrid-5-yl;

M preferably represents Cl, Br, tosyl or OSO₂OK, particularly preferably Cl or Br.

A very particularly preferred compound of the formula (I) is the compound of the formula (Ia)

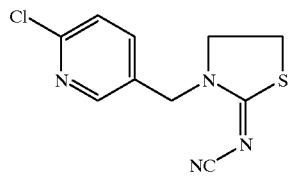

(Ia)

which is obtained by reacting the compound of the formula

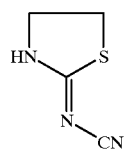

(IIa)

with the compound of the formula

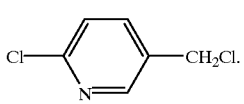

(IIIa)

In connection with alkyl, alkoxy, alkylthio or alkylsilyl groups, the term "lower" represents C₁–C₆-, preferably C₁–C₄-, alkyl, -alkoxy, -alkylthio or -alkylsilyl groups.

Particularly suitable polar protic solvents are water and alcohols or mixtures of water and alcohols. If the solvent used is an alcohol, which is preferred, the compounds of the formula (I) can be obtained directly in a modification that is advantageous for use as crop protection agents, and in the purity required.

Examples of alcohols which may be mentioned are:

primary alcohols, such as methanol, ethanol, propanol, butanol, 2-methyl-1-propanol, 1-pentanol, benzyl alcohol, secondary alcohols, such as isopropanol, sec-butanol, 2-pentanol, tert-alcohols, such as tert-butanol.

Particularly preferred solvents are alcohols which are not or are only partly water-miscible, such as iso-butanol or n-butanol or amyl alcohol, in particular n-butanol.

The process is, if appropriate, carried out in the presence of a base. Examples which may be mentioned are: alkali metal hydroxides and alkaline earth metal hydroxides, such as NaOH, KOH, Ca(OH)$_2$, alkali metal carbonates or bicarbonates, such as Na$_2$CO$_3$, Li$_2$CO$_3$, K$_2$CO$_3$, Cs$_2$CO$_3$ or NaHCO$_3$ and KHCO$_3$. K$_2$CO$_3$, NaOH and KHCO$_3$, in particular K$_2$CO$_3$, may be mentioned as being preferred.

The compounds of the general formula II can also be employed as alkali metal or alkaline earth metal salts, in solid or dissolved form.

If the reaction is carried out in water or water/alcohol mixtures, the process is carried out in a pH range between 8 and 13.

The catalysts used can be phase-transfer catalysts, if appropriate quaternary ammonium halides, such as tetrabutylammonium chloride etc.

The process can be carried out in a broad temperature range, for example between 30° C. and 100° C., preferably between 50° C. and 80° C. The reaction is advantageously carried out under atmospheric pressure; however, it can also be carried out under reduced or elevated pressure.

When carrying out the process in practice, for example 1 mol of the compounds of the formula (II) is reacted with from 1 to 1.3 mol, preferably from I to about 1.1 mol, of the compounds of the formula (III) at pH 8–9 in a polar solvent, such as butanol, in the presence of from 0.6 to 2 mol, preferably from 1 to 1.3 mol, of a base, such as potassium carbonate, and if appropriate in the presence of a catalyst, such as tetrabutylammonium chloride.

The reaction can also be carried out by initially charging the compounds of the general formula II as alkali metal salt or alkaline earth metal salt, in dissolved or suspended form, and metering in the compounds of the general formula III at reaction temperature.

The compounds of the formulae (II) and (III) are known from EP 0 235 725 (and the literature cited therein).

The compounds of the formula (I) are suitable, for example, for use as insecticides (EP A2 0235 752, EP A2 0259 738). The examples below illustrate the subject-matter of the invention, without limiting it in any way.

EXAMPLE 1

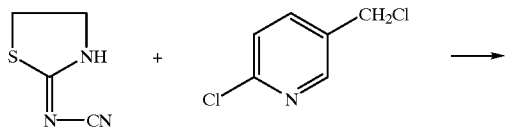

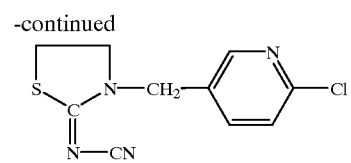

0.3 mol of 2-cyanoiminothiazolidine and 0.315 mol of 2-chloro-5-chloro-methyl-pyridine are dissolved in 240 g of n-butanol, and the solution is heated to 80° C. At this temperature, 0.36 mol of potassium carbonate are metered in, and the mixture is stirred at 80° C. for 2 h. After cooling (to 65° C.), 250 g of water are added and the phases are separated. The organic phase is then stirred at 50° C. for 3 h and subsequently cooled to 3° C. over a period of 3 h. Precipitated product is filtered off and dried; 62.3 g (83% of theory). M.p.: 135° C.

EXAMPLE 2

0.3 mol of 2-cyanoiminothiazolidine and 0.315 mol of 2-chloro-5-chloro-methyl-pyridine and 0.015 mol of tetrabutylammonium bromide are suspended in water, and the suspension is heated to 60° C. The pH of the reaction mixture is continuously maintained at from 8 to 8.5, using NaOH. After a reaction time of 2 h at 60° C., the phases are separated at this temperature and the organic phase is diluted with 200 ml of butanol and stirred at 50° C. for 3 h. Over a period of 3 h, the mixture is cooled to 3° C., and precipitated product is filtered off with suction; this gives 55.5 g (72% of theory).

EXAMPLE 3

39.3 g of 97% strength 2-cyanoimino-thiazolidine ($\underline{A}$ 0.3 mol) are taken up in 250 g of 80% strength n-butanol (containing 20% of H$_2$O) and admixed with 26.7 g of 45% strength aqueous sodium hydroxide solution (0.3 mol). This gives a pale-green solution which, at 65° C., is admixed with 49.5 g of 95% strength 2-chloro-5-chloromethylpyridine (0.29 mol). After a reaction time of 3.5 h, 190 g of water are added and the phases are separated. About 60 g of n-butanol/water are distilled off from the organic phase. The organic phase is then cooled to 50° C., seed crystals are added and cooling is continued to 0° C. At this temperature, the mixture is crystallized with stirring for 3 h. Filtration and drying give 61.8 g of 96% pure product (87% of theory).

What is claimed is:

1. Process for preparing compounds of the formula (I)

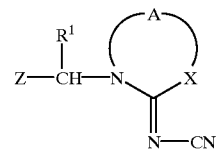

in which

R$^1$ represents a hydrogen atom or an alkyl group,

A represents an ethylene group, which may be substituted by alkyl, or a trimethylene group, which may be substituted by alkyl, X represents an oxygen or sulphur atom or the group

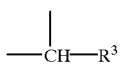

in which
R³ represents a hydrogen atom or an alkyl group, and
Z represents an optionally substituted 5- or 6-membered heterocyclic group which contains at least two heteroatoms selected from the group consisting of oxygen, sulphur and nitrogen atoms, or denotes an optionally substituted 3- or 4-pyridyl group,
characterized in that compounds of the formula (II)

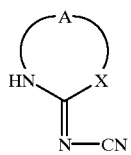
(II)

in which
A and X are each as defined above are reacted with compounds of the formula (III)

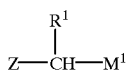
(III)

in which
R¹ and Z are each as defined above and
M¹ denotes a halogen atom or the group —OSO₂-M², in which M² denotes a lower alkyl group, an aryl group or OM³, where
M³ denotes a lower alkyl group or an alkali metal,
in the presence of a define solvent and, if appropriate, in the presence of a base.

2. Process according to claim 1, characterized in that the compound of the formula (Ia)

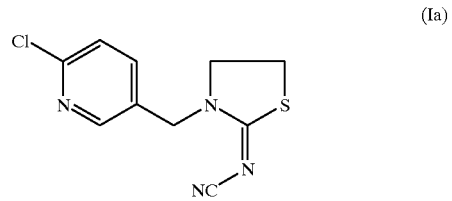
(Ia)

is obtained by reacting the compound of the formula

(IIa)

with the compound of the formula

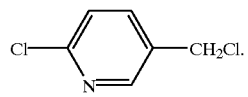
(IIIa)

* * * * *

UNITED STATES PATENT AND TRADEMARK OFFICE
CERTIFICATE OF CORRECTION

PATENT NO. : 6,211,379 B1　　　　　　　　　　　　　　　　　　　　　　　Page 1 of 1
DATED     : April 3, 2001
INVENTOR(S) : Hermann Seifert et al.

It is certified that error appears in the above-identified patent and that said Letters Patent is hereby corrected as shown below:

<u>Column 6,</u>
Line 4, the entire line should read as follows: "...in the presence of a protic solvent and, if appropriate, in the ...".

Signed and Sealed this

Fourteenth Day of May, 2002

*Attest:*

*Attesting Officer*

JAMES E. ROGAN
*Director of the United States Patent and Trademark Office*